United States Patent [19]
Warren et al.

[11] Patent Number: 5,886,204
[45] Date of Patent: Mar. 23, 1999

[54] PROCESS FOR THE PRODUCTION OF RUTHENIUM (III) ACETATE SOLUTION

[75] Inventors: Stephen Geoffrey Warren, Royston; Anthony Fulford, Mortimer, both of United Kingdom

[73] Assignee: BP Chemicals Limited, London, England

[21] Appl. No.: 969,664

[22] Filed: Nov. 13, 1997

Related U.S. Application Data

[60] Provisional application No. 60/031,823 filed Nov. 26, 1996.
[51] Int. Cl. $^6$ ................................................. C07F 15/00
[52] U.S. Cl. ............................................ 556/136; 502/170
[58] Field of Search .............................. 556/136; 502/170

[56] References Cited

U.S. PATENT DOCUMENTS 3,793,355 2/1974 Wilkinson ........................... 260/429 R

FOREIGN PATENT DOCUMENTS 63-315509 12/1988 Japan .

OTHER PUBLICATIONS

F.S. Martin, Journal of Chenical Society (London), pp. 2682–2684 Jul. 1952.

"$\mu_3$Oxo–triruthenium Carboxylate Complexes"; *J. Chem. Soc., Dalton*; A. Spencer & G. Wilkinson; Inorganic Chemistry Laboratories, Imperial College of Science & Technology, London, England; XP–002057663; ©1972; pp. 1570–1577.

"A Basic Trinuclear Ruthenium Acetate"; *J. Chem. Soc.*; F. S. Martin; London, England; XP–002057664; ©1952; pp. 2682–2684.

*Primary Examiner*—Porfirio Nazario-Gonzalez
*Attorney, Agent, or Firm*—Fay, Sharpe, Beall, Fagan, Minnich & McKee

[57] ABSTRACT

A process for the production of ruthenium (III) acetate solution which comprises reacting ruthenium (IV) oxide with a stoichiometric amount of a hydrazine reductant in the presence of acetic acid.

15 Claims, No Drawings

PROCESS FOR THE PRODUCTION OF RUTHENIUM (III) ACETATE SOLUTION

This application claims the benefit of U.S. Provisional Application Ser. No. 60/031,823, filed on Nov. 26, 1996.

The present invention concerns improvements in precious metal compounds. More especially, it concerns improvements in ruthenium compounds and methods for their production.

Ruthenium (III) acetate is the term that will be used herein to describe $[Ru_3O(OAc)_6(H_2O)_n(AcOH)_{3-n}]OAc$ where n has a value from 0 to 3, and the product of its desolvation, that is $[Ru_3O(OAc)_6]OAc$, and products consisting substantially of ruthenium (III) acetate, possibly in admixture with minor amounts of other ruthenium acetates, oxides and/or hydroxides. Ruthenium (III) acetate is a compound known per se and is available commercially, although it is not a bulk or commodity chemical. It may be used as a starting material for other ruthenium compounds, and its use has been suggested as a catalyst or catalyst precursor.

The generally accepted processes for the production of ruthenium (III) acetate involve reacting $RuCl_3.xH_2O$ with either acetic acid/acetic anhydride or sodium acetate in ethanol, but these routes suffer from rather poor yields and contamination of the product with other ruthenium species such as $[Ru_2(OAc)_4Cl]$ and with chloride and/or sodium ions. An alternative would be to react ruthenium (VIII) oxide with a mixture of acetic acid and a reductant such as acetaldehyde or ethanol. This latter reaction is hazardous owing to the explosive nature of ruthenium (VIII) oxide, although it could be expected to yield a high purity product. It is desirable to have alternative processes suited to the large scale, high yield preparation of ruthenium (III) acetate of high purity. The known processes tend to produce material contamination with impurities such as halide, which can contribute to plant and/or vessel corrosion, and undesired metallic impurities, which may contribute to a loss of selectivity in catalytic processes. Another undesirable impurity is sulfur, which is a well-known catalyst poison.

The present invention provides a process for the production of ruthenium (III) acetate solution in high yield and which comprises reacting ruthenium (IV) oxide with the stoichiometric amount of hydrazine reductant in the presence of acetic acid.

The process is desirably carried out in two steps, the first being reduction of ruthenium (IV) to ruthenium (III) by the hydrazine reductant in the presence of acetic acid, followed by heating, preferably at reflux, for an extended period, eg for 8–24 hours. The acetic acid reagent may be glacial acetic acid, but is preferably aqueous acetic acid, prepared by diluting glacial acetic acid with a small proportion of water, which readily permits the production of ruthenium (III) acetate solution of the preferred acetic acid composition.

Recommended hydrazine proportions are from 95 to 115% of the stoichiometric requirement. The stoichiometry of the reaction requires 1 mole of hydrazine to 4 moles of ruthenium, since hydrazine acts as a 4 electron reductant. The amount of hydrazine used should preferably be as close as possible to stoichiometric, to avoid significant over- or under-reduction of the ruthenium (IV) species. During the process, the hydrazine is converted to nitrogen gas, which escapes. The hydrazine is preferably used as an aqueous solution, but may be used as a neat liquid, or as a hydrazine salt in solid or solution form. The hydrazine reductant may be a substituted hydrazine, for example methylhydrazine, in which case the stoichiometry is altered. However, it is likely that this would generate unwanted by products from the substituted hydrazine, for example methylamine, which would contaminate the final product. For certain uses, such contamination may be unimportant.

It is believed that the reduction reaction may be described by the following equation:

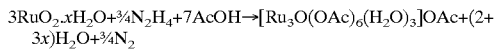

$3RuO_2.xH_2O+\frac{3}{4}N_2H_4+7AcOH\rightarrow[Ru_3O(OAc)_6(H_2O)_3]OAc+(2+3x)H_2O+\frac{3}{4}N_2$ The product may be desirably recovered as a solution by cooling the reaction mixture and removing any unreacted ruthenium (IV) oxide by filtration or centrifugation. It may be isolated as a solid by a variety of means obvious to those skilled in the art such as solution concentration, spray drying, or precipitation of the compound by treatment at low temperature or by addition of a suitable solvent.

The invention further provides ruthenium (III) acetate dissolved in aqueous acetic acid and containing low levels of impurities such as nitrogen (no greater than 200 ppm), halide (no greater than 50 ppm). Preferably, the solution contains no greater than 50 ppm of sulfur and no greater than 100 ppm of metallic impurities.

Most desirably, the acetic acid concentration is between 40 and 80 wt % and the ruthenium concentration between 4 and 8 wt %.

The starting material, hydrated ruthenium (IV) oxide is itself a known compound, but for the present invention is desirably prepared by the reduction of sodium ruthenate (VI) using an alcohol. The sodium ruthenate (VI) is a material known per se.

The present invention further extends to other ruthenium carboxylates which may be prepared in analogous manner to the acetate.

The invention is further described by way of example only in the following working example.

EXAMPLE 1

Hydrated ruthenium (IV) oxide (43.88 g) as prepared above was transferred to a 250 ml beaker and mixed well with glacial acetic acid (42.3 g), and transferred into a 250 ml round-bottomed flask equipped with a Teflon coated stirrer bar. The suspension was washed in with a further portion of glacial acetic acid (42.3 g) followed by water (9.0 g). The suspension was vigorously stirred then hydrazine (4.37 g of a 15.26 wt % solution in water) added slowly through a pipette over 10 minutes. The amount of hydrazine solution used was 110% of the stoichiometric proportion based on the estimated ruthenium content of the reaction mixture. There was a vigorous effervescence and a gradual temperature rise of about 15° C. The flask was fitted for reflux with a Liebig condenser and gently heated to reflux, which was continued for 21 hours, by which time the reaction mixture had become a dark green solution. Stirring was stopped and the flask allowed to cool and stand for 24 hours. The product was filtered through a 7 cm diameter glass fibre paper, yielding a clear, dark green product solution (141.0 g) containing 5.59 wt % of ruthenium as ruthenium (III). This corresponds to an overall yield of 98.5%. The product solution contained less than 50 ppm of halide and less than 100 ppm of nitrogen.

We claim:

1. A process for the production of ruthenium (III) acetate solution which comprises reacting ruthenium (IV) oxide with a stoichiometric amount of a hydrazine reductant in the presence of acetic acid.

2. A process as claimed in claim 1 comprising a first step of reducing ruthenium (IV) to ruthenium (III) by the hydrazine reductant in the presence of acetic acid and a second step of heating said ruthenium (III) for an extended period of time.

3. A process as claimed in claim 1 wherein the hydrazine reductant is present from 95 to 115% of stoichiometric amount.

4. A process as claimed in claim 1 wherein the ruthenium (III) is heated for 8 to 24 hours.

5. A solution of ruthenium acetate prepared according to a process as claimed in claim 1.

6. A solution as claimed in claim 5 wherein the ruthenium concentration is from 4 to 8 wt % and acetic acid concentration is from 40 to 80 wt %.

7. A process as claimed in claim 2 wherein the hydrazine reductant is present from 95 to 115% of stoichiometric amount.

8. A process as claimed in claim 2 wherein the ruthenium (III) is heated for 8 to 24 hours.

9. A process as claimed in claim 3 wherein the ruthenium (III) is heated for 8 to 24 hours.

10. A solution of high purity ruthenium acetate prepared according to a process as claimed in claim 2.

11. A solution of high purity ruthenium acetate prepared according to a process as claimed in claim 3.

12. A solution of high purity ruthenium acetate prepared according to a process as claimed in claim 4.

13. A solution as claimed in claim 10 wherein the ruthenium concentration is from 4 to 8 wt % and acetic acid concentration is from 40 to 80 wt %.

14. A solution as claimed in claim 11 wherein the ruthenium concentration is from 4 to 8 wt % and acetic acid concentration is from 40 to 80 wt %.

15. A solution as claimed in claim 12 wherein the ruthenium concentration is from 4 to 8 wt % and acetic acid concentration is from 40 to 80 wt %.

* * * * *